United States Patent
Shih et al.

(10) Patent No.: US 9,233,905 B2
(45) Date of Patent: Jan. 12, 2016

(54) OXIDATION AND CRYSTALLIZATION PROCESS FOR AROMATIC CARBOXYLIC ACID PRODUCTION

(71) Applicant: UOP LLC, Des Plaines, IL (US)

(72) Inventors: Raymond Shih, Elgin, IL (US); Alakananda Bhattacharyya, Glen Ellyn, IL (US); Carl J Stevens, Lake Forest, IL (US); Joel T. Walenga, Lake Zurich, IL (US)

(73) Assignee: UOP LLC, Des Plaines, IL (US)

( * ) Notice: Subject to any disclaimer, the term of this patent is extended or adjusted under 35 U.S.C. 154(b) by 61 days.

(21) Appl. No.: 13/715,620

(22) Filed: Dec. 14, 2012

(65) Prior Publication Data

US 2014/0171679 A1    Jun. 19, 2014

(51) Int. Cl.
*C07C 51/265* (2006.01)
*C07C 51/43* (2006.01)

(52) U.S. Cl.
CPC ............ *C07C 51/265* (2013.01); *C07C 51/43* (2013.01)

(58) Field of Classification Search
None
See application file for complete search history.

(56) References Cited

U.S. PATENT DOCUMENTS

| | | | |
|---|---|---|---|
| 7,985,875 B2 | 7/2011 | Hashmi et al. | |
| 2002/0183546 A1 | 12/2002 | Sheppard | |
| 2004/0015009 A1* | 1/2004 | Earle et al. | 562/409 |
| 2009/0326265 A1* | 12/2009 | Hashmi et al. | 562/416 |
| 2010/0174111 A1 | 7/2010 | Rogers et al. | |
| 2012/0004449 A1 | 1/2012 | Bhattacharyya et al. | |
| 2012/0004450 A1 | 1/2012 | Bhattacharyya et al. | |
| 2012/0004456 A1 | 1/2012 | Bhattacharyya et al. | |

FOREIGN PATENT DOCUMENTS

| JP | 2004231636 A | 8/2004 |
|---|---|---|
| JP | 2004231636 A2 | 8/2004 |

OTHER PUBLICATIONS

Liu et al., "Hydrolysis reaction of poly(ethylene terephthalate) using ...," Journal of Applied Polymer Science, v 114, n 6, Dec. 15, 2009, pp. 3561-3565.
Subramaniam, Bala, "Exploiting Neoteric Solvents for Sustainable ...," Ind. Eng. Chem. Res. 2010, 49, pp. 10218-10229.
Zhou et al., "Effective catalysis of poly(ethylene terephthalate) (PET) degradation ...," Pure Appl. Chem., V 84, No. 3, 2012, pp. 789-801.
PCT International Search Report dated Apr. 10, 2014 for PCT/US2013/071821.

* cited by examiner

*Primary Examiner* — Sudhakar Katakam
*Assistant Examiner* — Jennifer C Sawyer

(57) ABSTRACT

A process for oxidizing and crystallizing alkyl aromatics is described. The solvent and operating conditions are controlled to maintain the aromatic carboxylic acid in solution in the reaction zone, and the aromatic carboxylic acid is crystallized in a downstream crystallizer, resulting in reduced impurity levels in the product.

18 Claims, 4 Drawing Sheets

OXIDATION AND CRYSTALLIZATION PROCESS FOR AROMATIC CARBOXYLIC ACID PRODUCTION

FIELD OF THE INVENTION

This invention relates to processes useful for oxidizing alkyl aromatic compounds. More particularly, the invention relates to the oxidation and crystallization process resulting in lower levels of impurities in the product.

BACKGROUND OF THE INVENTION

Oxidation of alkyl aromatic compounds, e.g., toluene and xylenes are important commercial processes. A variety of oxidation products may be obtained including aromatic carboxylic acids such as terephthalic acid (1,4-benzenedicarboxylic acid) and isophthalic acid (1,3-benzenedicarboxylic acid) which are used, for example, in the polymer industry.

It is known that oxidation products, such as aromatic alcohols, aromatic aldehydes, aromatic ketones, and aromatic carboxylic acids, may solidify or crystallize at oxidation conditions and/or as the reaction mixture cools. Thus, mixtures of oxidation products may be produced which require further processing to increase the purity of the desired product. For example, in the production of terephthalic acid, the oxidation product is often referred to as crude terephthalic acid because it contains impurities including color bodies and intermediate oxidation products, especially 4-carboxybenzaldehyde (4-CBA). To obtain polymer grade or purified terephthalic acid, various purification steps are known in the art including: washing the crude terephthalic acid with water and/or a solvent, additional oxidation or crystallization steps, and reacting a solution of dissolved crude terephthalic acid with hydrogen at hydrogenation conditions usually including a catalyst comprising palladium and carbon. Often several purification steps are used.

U.S. Pat. No. 2,833,816 discloses processes for oxidizing aromatic compounds to the corresponding aromatic carboxylic acids. A process for the liquid phase oxidation of alkyl aromatic compounds uses molecular oxygen, a metal or metal ions, and bromine or bromide ions in the presence of an acid. The metals may include cobalt and/or manganese. Exemplary acids are lower aliphatic mono carboxylic acids containing 1 to 8 carbon atoms, especially acetic acid.

U.S. Pat. No. 6,355,835 discloses a process for the preparation of benzene dicarboxylic acids by liquid phase oxidation of xylene isomers using oxygen or air by oxidizing in the presence of acetic acid as a solvent, a cobalt salt as a catalyst, and an initiator. The oxidation step is followed by flashing the reaction mixture to remove volatile substances and cooling and filtering the material to get crude benzene di-carboxylic acid as a solid product and a filtrate. Recrystallizing the crude benzene di-carboxylic acid to obtain at least 99% purity and recycling of the filtrate are also disclosed.

U.S. Pat. No. 7,094,925 discloses a process for preparing oxidation products of alkyl-aromatic compounds. The process includes mixing an oxidizing agent or sulfur compound in the presence of an ionic liquid. Air, dioxygen, peroxide, superoxide, or any other form of active oxygen, nitrite, nitrate, and nitric acid or other oxides or oxyhalides of nitrogen (hydrate or anhydrous) can be used as the oxidizing agent. The process is typically carried out under Bronstead acidic conditions. The oxidation is preferably performed in an ionic liquid containing an acid promoter, such as methanesulfonic acid. The product is preferably a carboxylic acid or ketone or intermediate compound in the oxidation, such as an aldehyde, or alcohol.

U.S. Pat. No. 7,985,875 describes a process for preparing an aromatic polycarboxylic acid by liquid phase oxidation of a di- or tri-substituted benzene or naphthalene compound. The process involves contacting the aromatic compound with an oxidant in the presence of a carboxylic acid solvent, a metal catalyst, and a promoter in a reaction zone. The promoter is an ionic liquid comprising an organic cation and a bromide or iodide anion. The promoter is used in a concentration range of about 10 to about 50,000 ppm (based on solvent) with a preferred range of 10-1,000 ppm. No other promoters, such as bromine-containing compounds, need to be used in the process. The process produces crude terephthalic acid (CTA) having 1.4-2.2% 4-CBA. Purification of the CTA is required to obtain purified terephthalic acid (PTA).

US 2010/0174111 describes a process for purifying aryl carboxylic acids, such as terephthalic acid. The impure acid is dissolved or dispersed in an ionic liquid. A non-solvent (defined as a molecular solvent for which the ionic solvent has high solubility and for which the aryl carboxylic acid has little or no solubility) is added to the solution to precipitate the purified acid.

U.S. Pat. No. 7,692,036, 2007/0155985, 2007/0208193, and 2010/0200804 disclose a process and apparatus for carrying out the liquid-phase oxidation of an oxidizable compound. The liquid phase oxidation is carried out in a bubble column reactor that provides for a highly efficient reaction at relatively low temperatures. When the oxidized compound is para-xylene, the product from the oxidation reaction is CTA which must be purified. Purification is said to be easier than for conventional high temperature processes.

SUMMARY OF THE INVENTION

One aspect of the invention is a process for oxidizing an alkyl aromatic compound. In one embodiment, the process includes contacting the alkyl aromatic compound, a first solvent, a first bromine source, a first catalyst, and a first oxidizing agent in a first reaction zone at a temperature of about 240° C. or less and a pressure in a range of about 0.69 MPa(g) (100 psig) to about 4.1 MPa(g) (600 psig) for less than about 90 min to produce a first oxidation product comprising aromatic carboxylic acid, and at least one of unoxidized alkyl aromatic compound or partially oxidized alkyl aromatic compound, at least 50% of the aromatic carboxylic acid remaining in solution. The first oxidation product is introduced into a first crystallization zone, and a composition of solvent in the first crystallization zone is controlled to maintain the partially oxidized alkyl aromatic compound in solution. At least a portion of the aromatic carboxylic acid in the first crystallization zone is crystallized to produce a first crystallized aromatic carboxylic acid and a first mother liquor comprising the first crystallization zone solvent and the at least one of unoxidized alkyl aromatic compound or partially oxidized alkyl aromatic compound and optionally aromatic carboxylic acid in solution, the first crystallization zone being at a temperature of about 220° C. or less and a pressure in a range of about 0 MPa(g) (0 psig) to about 2.1 MPa(g) (300 psig).

DETAILED DESCRIPTION OF THE INVENTION

Figure 1:
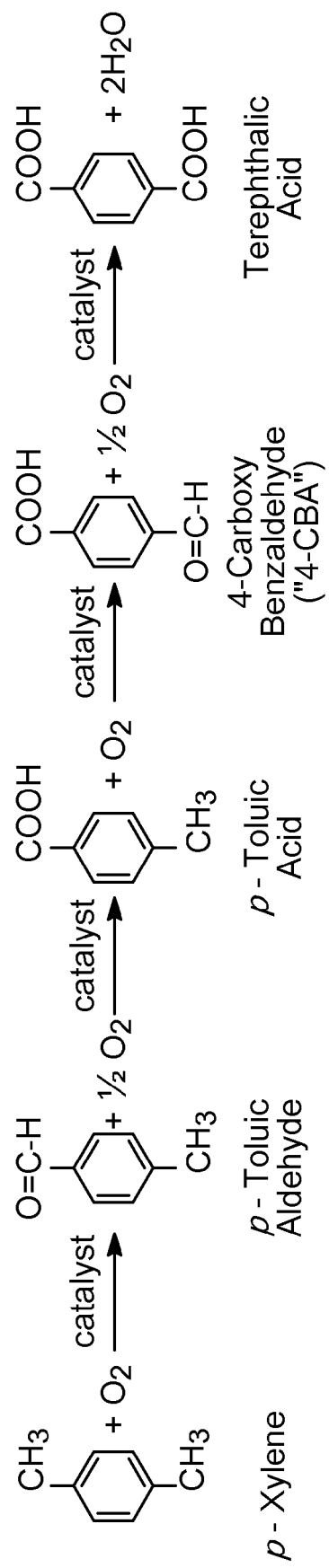
FIG. 1 is a reaction scheme for the oxidation of p-xylene.

The process involves oxidizing alkyl aromatic compounds and crystallizing aromatic carboxylic acid to produce a product having a lower level of impurities. By controlling the amount and composition of the solvent and the operating conditions in the oxidation zone and crystallization zone, the impurities can be maintained in solution while crystallizing the aromatic carboxylic acid, leading to lower levels of impurities in the product.

Although the following discussion focuses on the oxidation of para-xylene to terephthalic acid for the sake of convenience, the process is not limited. Other alkyl aromatic compounds can be used, as discussed below.

In a conventional purified terephthalic acid process, the oxidation section includes one or several continuously stirred-tank reactors (CSTR), followed by crystallizers and washer/separators. CSTR is widely used to accommodate excessive crystallization of terephthalic acid in the reactor. By selecting solvents having higher solubility of terephthalic acid, crystallization can be controlled. The solvent should also have better partition factors for the main impurity, 4-CBA. The process can be significantly improved if solvents with these behaviors are used.

The process involves a number of differences from conventional processes. Crystallization within the oxidation reactor is limited by controlling the solubility of the terephthalic acid in the solvent and by controlling generation of the terephthalic acid product. With higher solubility, more terephthalic acid is expected to exist in the liquid phase. Generally, more than 50% of the terephthalic acid formed in the first oxidation zone is maintained in solution exiting the first oxidation zone, or more than 60%, or more than 70%, or more than 75%, or more than 80%, or more than 85%, or more than 90%, or more than 95%, or more than 97%, or more than 99%. By delaying crystallization to a downstream crystallizer(s) and optional additional oxidizer(s), impurities can be controlled significantly better than in conventional processes.

The strong physical property of the ionic liquid solvent system can significantly improve product purity by minimizing impurity co-crystallization from the final terephthalic acid product. Unlike conventional processes where a significant amount of terephthalic acid was crystallized in the reactor with various impurities co-precipitated, the present process can reduce crystallization in the reactor, and further lower co-crystallization in the crystallizers.

The process is optimized for ionic liquid solvent or other solvent with similar behavior. Although the following discussion focuses on ionic liquid solvents, other solvents having the desired properties can be also used.

The solvent composition is controlled for each operation (e.g., first and second reactors, first and second crystallizers etc.) including the ionic liquid solvent composition and its ratio to the acetic acid solvent. In the reactor, an appropriate solvent composition can reduce the impurity concentration in the liquid and crystallized phases. In the crystallizers, an appropriate solvent composition can minimize the impurity co-crystallization. The compositions can be individually controlled through the addition of solvent stream(s) before the operation.

Figure 2:
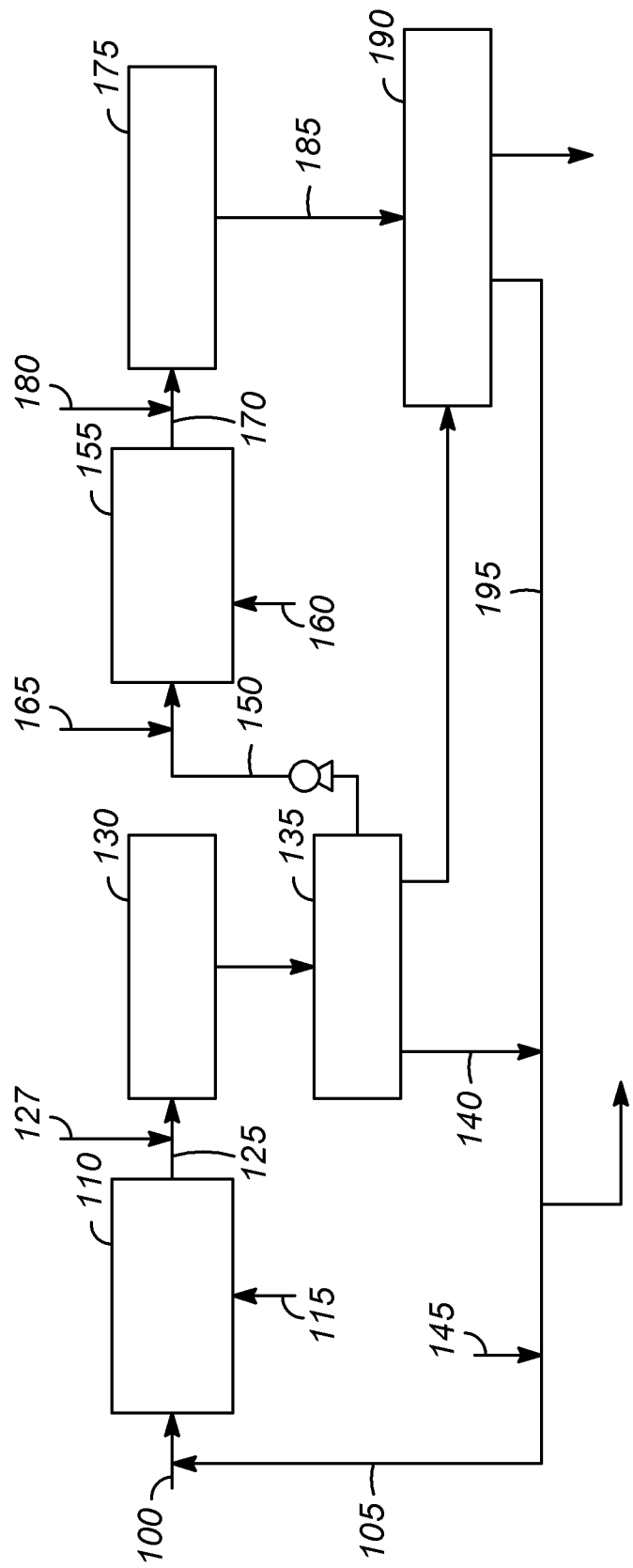
FIG. 2 is a general process flow diagram for one embodiment of a process for producing oxidized alkyl aromatic compounds.

One embodiment includes continuous stirred tank reactors (CSTRs) in the process, as shown in FIG. 2. Contrary to a conventional xylene oxidation process that generally allows the reaction to proceed close to completion in the oxidation reactor, this process limits the reaction completion so that none or only a small fraction of the terephthalic acid crystal is present in the reactor. The goal is to keep the impurity in the final product so that it meets the specification. Therefore, the amount crystallized in the reactor is controlled based on the degree of impurity co-crystallization in both the reactors and the crystallizers, and on the reactor operating conditions which affect solubility and partition factor.

In FIG. 2, a feed stream 100 containing p-xylene and solvent, along with recycled mother liquor stream 105, enters the reactor 110 and mixes with air or enriched oxygen 115.

Reactor 110 is operated at a temperature of about 240° C. or less, or in a range of about 150° C. to about 240° C., or about 170° C. to about 240° C., or about 200° C. to about 220° C. The pressure is generally in a range of about 0.69 MPa(g) (100 psig) to about 4.1 MPa(g) (600 psig), or about 1.4 MPa(g) (200 psig).

The residence time is controlled to allow limited terephthalic acid conversion and crystallization in order to adjust the final product quality. The residence time is generally less than 90 min, or less than 60 min, or less than 45 min, or less than 30 min.

The solvent comprises ionic liquid solvent, and acetic acid solvent. The ionic liquid solvent includes one or more ionic liquids and ionic solid if present.

The ionic liquid solvent to acetic acid solvent ratio inside reactor has to be carefully controlled for optimum solubility and productivity. The reactor effluent can be tested to determine the ratio of ionic liquid solvent to acetic acid solvent, and the ratio can be controlled through the recycle, reflux, and fresh make-up streams. The typical ratio is 1, but it can vary from 0.1 to 10 depending on the operating conditions.

A vapor stream containing mainly oxygen-deprived air, water, and acetic acid is cooled in an overhead condenser. Water and acetic acid are condensed and refluxed to the reactor 110 to control the reactor temperature, with a stream drafted to control water concentration in reactor 110.

Effluent stream 125, containing little or no precipitated terephthalic acid, enters a crystallizer(s) 130 and separator 135 to provide direct recycle of mother liquor to the reactor 110. The effluent stream 125 contains less than 50% precipitated terephthalic acid, or less than 40%, or less than 30%, or less than 20%, or less than 15%, or less than 10%, or less than 5%.

The solvent concentration in the crystallizer 130 can be adjusted using solvent makeup stream 127.

The temperature of the crystallizer 130 is generally at least 10° C., or at least 20° C. less than the temperature of the reactor 110. The crystallizer 130 is generally at a temperature of about 220° C. or less, or about 100° C. to about 220° C., or about 150° C. to about 220° C., or about 180° C. to about 200° C. The pressure is generally in a range of about 0 MPa(g) (0 psig) to about 2.1 MPa(g) (300 psig), or 0 MPa(g) (0 psig) to about 2.1 MPa(g) (300 psig).

Recycle stream 140 containing ionic liquid solvent and acetic acid mixes with make-up ionic liquid solvent 145 to form recycle mother liquor stream 105 which returns to the reactor 110 to maintain the optimum solvent ratio for higher solubility and lower impurity co-crystallization.

Product stream 150 entering an optional secondary reactor 155 is contacted by air or oxygen stream 160 for further oxidation reaction in an optimized solvent ratio through adjustment of the solvent make-up stream 165. The typical ratio is 1, but it can vary from 0.1 to 10 depending on the operating conditions. The secondary reactor 155 is generally at the same or a lower temperature as the first reactor 110. The temperature is typically about 240° C. or less, or in a range of about 150° C. to about 240° C., or about 180° C. to about 240° C., or about 200° C. to about 220° C. The pressure is generally about 0.69 MPa(g) (100 psig) to about 4.1 MPa(g) (600 psig), or about 1.4 MPa(g) (200 psig). The residence time is generally less than 90 min, or less than 60 min, or less than 45 min, or less than 30 min.

The effluent from the secondary reactor 170 enters a second crystallizer(s) 175 with additional fresh ionic liquid solvent stream 180. The second crystallizer is generally at a temperature in a range of about 70° C. to about 200° C. The pressure is generally in a range of about 0 MPa(g) (0 psig) to about 2.1 MPa(g) (300 psig).

The solvent composition is controlled for optimum partition in order to minimize the impurities co-precipitated with solid terephthalic acid. The typical ratio is 1, but it can vary from 0.1 to 10 depending on the operating conditions.

The effluent 185 from the crystallizer 175 enters the separators 190. Suitable separators include, but are not limited to, cyclones, filters, centrifuges, or combinations thereof. Terephthalic acid is separated from the bulk mother liquor and goes to an additional washing and separation stage. The cooler mother liquor 195, containing ionic liquid solvent, excess acetic acid, and intermediate reaction products, re-enters the reactor for further reaction and assists in quenching. Additional ionic liquid or acetic acid solvent can be added, if necessary.

Figure 3:
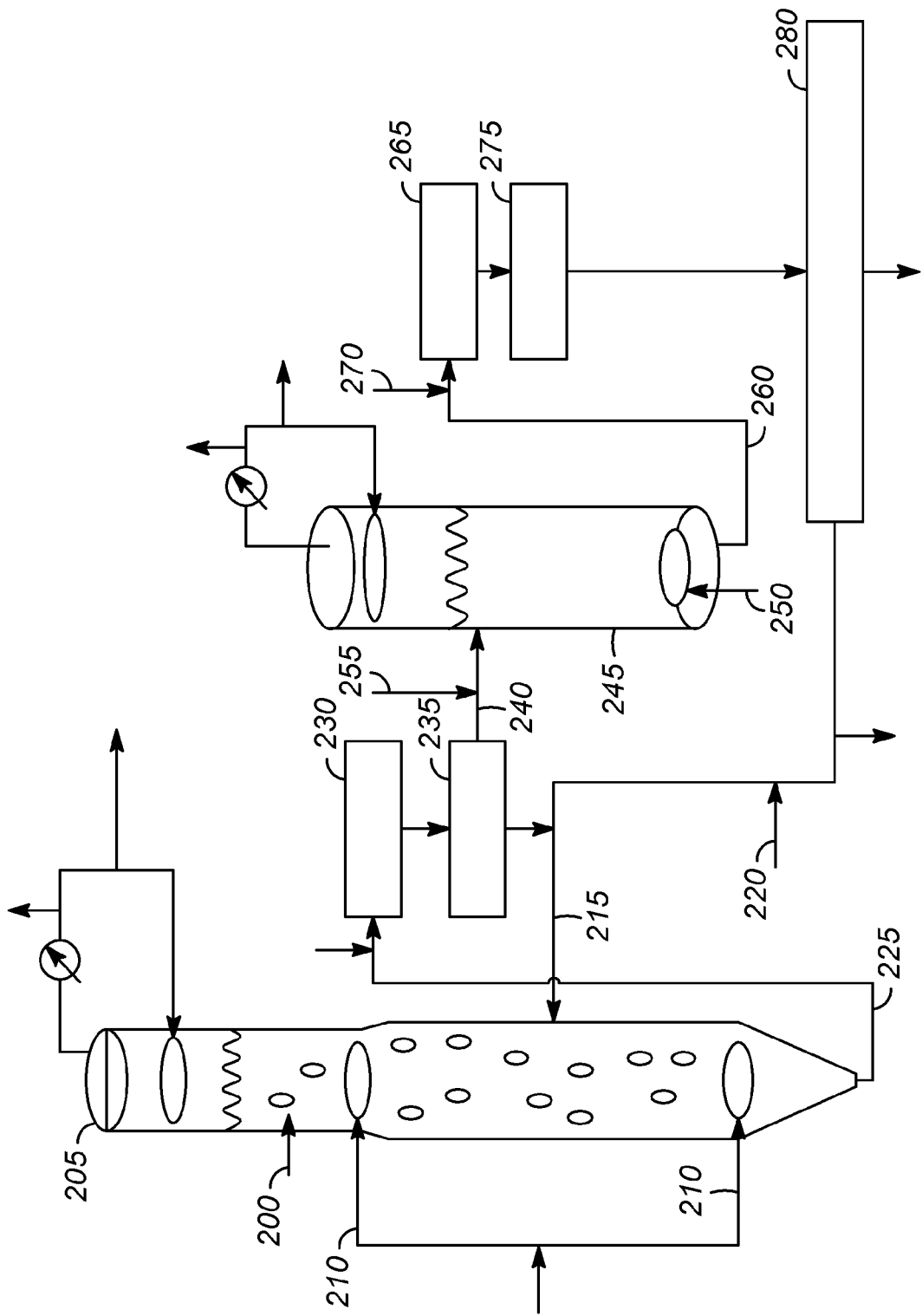
FIG. 3 is a general process flow diagram for another embodiment of a process for producing oxidized alkyl aromatic compounds.

The second process includes a plug-flow reactor, as shown in FIG. 3. The design shows a down-flow reactor, but it can be modified for upward flow. The design also shows that ionic liquid solvent can be introduced at a later stage so only acetic acid is used as the solvent in the initial stage but at lower solvent-to-feed ratio. This is to take advantage of higher productivity converting p-xylene to p-toluic acid. This design can be modified to add ionic liquid solvent together with feed and acetic acid to maintain common solvent-to-feed ratio throughout the reactor.

As shown in FIG. 3, a feed stream 200 containing p-xylene and acetic acid enters the reactor 205 and mixes with air or enriched oxygen 210. There can be more than one feed entry point, if desired. At a lower solvent-to-feed ratio, the reaction is allowed to proceed to convert most p-xylene to p-toluic acid or other intermediates, before mixing with recycled mother liquor stream 215. By adjusting the recycle stream 215 and make-up stream 220, the ionic liquid solvent to acetic acid solvent ratio can be carefully controlled for optimum solubility and productivity. The typical ratio is 1, but it can vary from 0.1 to 10 depending on the operating conditions. The solvent-to-reactant ratio after mixing is higher than at the initial stage without ionic liquid solvent.

The recycle stream 215 enters at a temperature lower than the reactor temperature to assist with cooling. The vapor stream, containing mainly oxygen-deprived air, water, and acetic acid, is cooled in an overhead condenser. Water and acetic acid are condensed and refluxed to the reactor 205 to control the reactor temperature through reflux distributor, with a small amount drafted to control water concentration in the reactor 205.

The effluent stream 225 containing little or no precipitated terephthalic acid enters a crystallizer 230 and a separator 235 to provide direct recycle of mother liquor 215 to the reactor 205. As discussed above, the crystallizer can effectively reduce the terephthalic acid concentration in the liquid before returning to the reactor to allow more reaction. The recycle stream 215, containing ionic liquid solvent and of acetic acid solvent, mixes with make-up ionic liquid solvent and returns to the reactor for the optimum solvent ratio for higher solubility and lower impurity co-crystallization. The product stream 240 entering an optional secondary reactor 245 is contacted by an air or oxygen stream 250 for further oxidation reaction in an optimized solvent ratio through adjustment of the solvent make-up stream 255. The optional secondary reactor 245 can also assist with product purity by allowing more residence time for co-crystallized 4-CBA to be re-dissolved in mother liquor. It is not necessary to drive oxidation reaction towards completion. Most intermediate reactants are expected to return to the main reactor in the recycle stream.

The effluent from the secondary reactor 245 enters the crystallizer(s) 265 with additional fresh solvent stream 270. The solvent composition is controlled for optimum partition in order to minimize the impurity co-precipitated with solid terephthalic acid. The effluent from the crystallizer 265 enters the separators 275, which can be, but are not limited to, cyclones, filters, centrifuges, or combinations thereof. Terephthalic acid is separated from the bulk mother liquor and goes to an additional washing and separation stage 280. The cooler mother liquor 215, containing mainly ionic liquid solvent, excess acetic acid, and intermediate reaction products, re-enters the reactor 205 for further reaction and assists in quenching. Additional ionic liquid or acetic acid solvent 220 can be added, if necessary.

The contacting step(s) may be practiced in laboratory scale experiments through full scale commercial operations. The process may be operated in batch, continuous, or semi-continuous mode. The contacting step can take place in various ways. The order of addition of the components (e.g., alkyl-aromatic compound, solvent, bromine source, catalyst, and oxidizing agent) is not critical. For example, the components can be added individually, or two or more components may be combined or mixed before being combined or mixed with other components.

Suitable alkyl aromatic compounds or feeds to be oxidized include aromatic compounds comprising at least one benzene ring having at least one alkyl group. Methyl, ethyl, and iso-propyl alkyl groups are preferred alkyl groups, although other alkyl groups can be used if desired. In an embodiment, the alkyl aromatic compound is selected from toluene, para-xylene, ortho-xylene, and meta-xylene. The feed may comprise more than one alkyl aromatic compound. As the oxidation reaction generally proceeds through successive degrees of oxidization, suitable feed compounds also include partially oxidized intermediates relative to the desired oxidized product. For example, in the production of terephthalic acid, the alkyl aromatic feed may comprise para-toluic acid and/or 4-carboxybenzaldehyde (4-CBA).

In some embodiments, the solvent comprises at least one ionic liquid. Two or more ionic liquids can be used, if desired.

Generally, ionic liquids are non-aqueous, organic salts composed of ions where the positive ion is charge balanced with a negative ion. These materials have low melting points, often below 100° C., undetectable vapor pressure, and good chemical and thermal stability. The cationic charge of the salt is localized over hetero atoms, and the anions may be any inorganic, organic, or organometallic species.

Most ionic liquids are formed from cations that do not contain acidic protons. The synthesis of ionic liquids can generally be split into two parts: formation of the desired cation, and anion exchange to form the desired product. Quaternization of an amine or phosphine, for example, is the initial step in the synthesis of the cation of an ionic liquid. If it is not possible to form the desired anion directly by the quaternization reaction, a further step is required.

Cations and anions for ionic liquids are described in US Publication 2010/0174111, for example.

The organic cation can comprise a linear, branched, or cyclic heteroalkyl unit. The term "heteroalkyl" refers to a cation comprising one or more heteroatoms chosen from nitrogen, oxygen, sulfur, boron, arsenic, boron, antimony, aluminum, or phosphorous capable of forming a cation. The heteroatom can be a part of a ring formed with one or more other heteroatoms, for example, pyridinyl, imidazolinyl rings, that can have substituted or unsubstituted linear or branched alkyl units attached thereto. In addition, the cation can be a single heteroatom wherein a sufficient number of substituted or unsubstituted linear or branched alkyl units are attached to the heteroatom such that a cation is formed.

Non-limiting examples of heterocyclic and heteroaryl units that can be alkylated to form cationic units include imidazole, pyrazoles, thiazoles, isothiazoles, azathiozoles, oxothiazoles, oxazines, oxazolines, oxazaboroles, dithiozoles, triazoles, selenozoles, oxaphospholes, pyrroles, boroles, furans, thiphenes, phospholes, pentazoles, indoles, indolines, oxazoles, isothirazoles, tetrazoles, benzofuran, dibenzofurans, benzothiophenes, dibenzothiophenes, thiadiazoles, pyrdines, pyrimidines, pyrazines, pyridazines, piperazines, piperidines, morpholines, pyrans, annolines, phthalazines, quinazolines, and quinoxalines.

The anionic portion of the ionic liquid can comprise an inorganic, organic, or organometallic moiety. Non-limiting examples of anions include inorganic anions: halides, (e.g., F, Cl, Br, and I); borides, $BX_4$, wherein X represents halogen, (e.g., $BF_4$, $BCl_4$), and the like; phosphates(V), $PX_6$; $PF_6$, and the like; arsenate(V), $AsX_6$; $AsF_6$, and the like; stibate(V) (antimony), $SbX_6$; $SbF_6$, and the like; $CO_3^{2-}$; $NO_2^{1-}$, $NO_3^{1-}$, $SO_4^{2-}$, $PO_4^{3-}$, $(CF_3)SO_3^{1-}$, and combinations and derivatives thereof.

Other non-limiting examples of ionic liquid anions include substituted azolates, that is, five membered heterocyclic aromatic rings that have nitrogen atoms in either positions 1 and 3 (imidazolates); 1, 2, and 3 (1,2,3-triazolates); or 1, 2, 4 (1,2,4-triazolate). Substitutions to the ring occur at positions that are not located in nitrogen positions (these are carbon positions) and include CN (cyano-), $NO_2$ (nitro-), and $NH_2$ (amino) group appended to the heterocyclic azolate core.

Further non-limiting examples of anions include substituted or unsubstituted borides: $B(R)_4$; substituted or unsubstituted sulfates: $(RO)S(=O)_2O$; substituted or unsubstituted acyl units $RCO_2$, for example, acetate $CH_3CO_2$, proprionate, $CH_3CH_2CO_2$, butyrate $CH_3CH_2CH_2CO_2$, and benzylate, $C_6H_5CO_2$; substituted or unsubstituted phosphates: $(RO)_2P(=O)O$; substituted or unsubstituted carboxylates: $(RO)C(=O)O$; substituted or unsubstituted azolates wherein the azolate can be substituted on a carbon atom by a unit chosen from cyano, nitro, and amino. R can be an organic, inorganic, or organometallic group. Non-limiting examples of R include hydrogen; substituted or unsubstituted linear branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; and seleno.

In an embodiment, ionic liquids suitable for use include, but are not limited to, one or more of imidazolium ionic liquids, pyridinium ionic liquids, tetra alkyl ammonium ionic liquids, and phosphonium ionic liquids. More than one ionic liquid may be used. Imidazolium, pyridinium, and ammonium ionic liquids have a cation comprising at least one nitrogen atom. Phosphonium ionic liquids have a cation comprising at least one phosphorus atom. In an embodiment, the ionic liquid comprises a cation selected from alkyl imidazolium, di-alkyl imidazolium, and combinations thereof. In another embodiment, the ionic liquid comprises an anion selected from halides, acetate, carboxylates, and combinations thereof. The ionic liquid may comprise at least one of 1-butyl 3-methyl imidazolium acetate (BMImOAc), 1-butyl 3-methyl imidazolium bromide (BMImBr), 1-hexyl 3-methyl imidazolium acetate (C6MImOAc), and 1-hexyl 3-methyl imidazolium bromide (C6MImBr).

The ionic liquid can be provided, or it can be generated in situ from appropriate precursors, or both. If it is generated in situ, the solvent comprises precursors of one or more ionic liquids. The ionic liquid precursors comprise a cation precursor, such as an alkyl imidazole, alkyl pyridine, alkyl amine, alkyl phosphine, and the like, and an anion precursor, such as alkyl or aryl halides or acetates. In an embodiment, the precursors are methyl imidazole and butyl bromide.

The mode of introducing the ionic liquid precursors may vary depending on the nature of the alkyl aromatics being oxidized and the nature and purity of the product desired. In one mode of addition, the cation precursors and the anion precursors (generally liquids at room temperature and pressure) are mixed with a carboxylic acid (for example, acetic acid) solvent and introduced into the oxidation reactor(s). In another mode of addition, the ionic liquid precursors may be mixed with the alkyl aromatic feed and introduced into the oxidation reactors. In another mode of addition, both cation and anion ionic liquid precursor components may be introduced into the bottom of the reactor without pre-mixing with any other oxidation reactor components such as the feed, carboxylic acid solvent, and catalyst package.

The solvent can also comprise a carboxylic acid. When carboxylic acids are used in the solvent, the amount of carboxylic acid is decreased compared with conventional processes in order to avoid excessive solvent volumes. The carboxylic acid desirably has from 1 to 7 carbon atoms. In an embodiment, the carboxylic acid comprises acetic acid. The solvent may contain more than one carboxylic acid. For example, the solvent may further comprise benzoic acid. In another embodiment, the carboxylic acid of the solvent is acetic acid.

In an embodiment, the solvent has a ratio of the ionic liquid solvent to the carboxylic acid solvent within a range of about 0.1:1 to 10:1 by weight. The amount of ionic liquid includes ionic liquid precursors, if present. The optional ionic solid or material capable of forming an ionic salt in solution discussed below, if present, is included in the amount of ionic liquid.

Optionally, an ionic solid, such as ammonium acetate ($NH_4OAc$) and/or ammonium bromide ($NH_4Br$), can be added to the mixture. Alternatively, a material which is capable of forming an ionic salt in solution can be added. The material can form the ionic salt in solution by combining with ions present in the solution. For example, in a solution containing bromide (for example in the form of HBr) or acetate ions (for example, in the form of acetic acid), ammonia could combine with the bromide or acetate ions forming ammonium bromide or ammonium acetate. The use of one or more ionic solids or materials capable of forming an ionic salt in solution provided an additional reduction in the level of impurities.

In an embodiment, the amount of ionic solid and material capable of forming an ionic salt in solution ranges from about 5 wt % to about 45 wt %, relative to the weight of the solvent, or from about 10 wt % to about 45 wt %, relative to the weight of the solvent. The solvent includes the carboxylic acid, the ionic liquid and/or ionic liquid precursors, the optional ionic solid or material capable of forming an ionic salt in solution, the optional water.

Optionally, the solvent may further comprise water. The water may be added to the mixture or generated in the mixture during the oxidation process.

In an embodiment, the ratio of solvent to alkyl-aromatic compound in the mixture ranges from about 1:1 to about 10:1 by weight, or from about 1.5:1 to about 6:1 by weight, or from about 2:1 to about 4:1 by weight. The solvent includes the carboxylic acid, the ionic liquid and/or ionic liquid precursor, the optional ionic solid or material capable of forming an ionic salt in solution, the optional water.

The catalyst comprises at least one of cobalt, manganese, titanium, chromium, copper, nickel, vanadium, iron, molybdenum, tin, cerium and zirconium. In an embodiment, the catalyst comprises cobalt and manganese. The metal may be in the form of an inorganic or organic salt. For example, the metal catalyst may be in the form of a carboxylic acid salt, such as, a metal acetate and hydrates thereof. Exemplary catalysts include cobalt (II) acetate tetrahydrate and manganese (II) acetate, individually or in combination. In an embodiment, the amount of manganese (II) acetate is less than the amount of cobalt (II) acetate tetrahydrate by weight.

The amount of catalyst used in the invention may vary widely. For example, the amount of cobalt may range from about 0.001 wt % to about 2 wt % relative to the weight of the solvent. In an embodiment, the amount of cobalt ranges from about 0.05 wt % to about 2 wt % relative to the weight of the solvent. The amount of manganese may range from about 0.001 wt % to about 2 wt % relative to the weight of the solvent. In an embodiment, the amount of manganese ranges from about 0.05 wt % to about 2 wt % relative to the weight of the solvent. In another embodiment, the ratio of cobalt to manganese ranges from about 3:1 to about 1:2 by weight on an elemental metal basis.

Bromine sources are generally recognized in the art as being catalyst promoters and include bromine, ionic bromine, e.g. HBr, NaBr, KBr, $NH_4Br$; and/or organic bromides which are known to provide bromide ions at the oxidation conditions, such as, benzylbromide, mono and di-bromoacetic acid, bromoacetyl bromide, tetrabromoethane, ethylene dibromide. In an embodiment, the bromine source comprises or consists essentially of or consists of hydrogen bromide. The amount of hydrogen bromide may range from about 0.01 wt % to about 5 wt %, relative to the weight of the solvent. In another embodiment, the amount of hydrogen bromide ranges from about 0.05 wt % to about 2 wt %, relative to the weight of the solvent. The solvent includes the carboxylic acid, the ionic liquid, the ionic liquid precursors, the optional ionic solid or material capable of forming an ionic salt in solution, the optional water.

Suitable oxidizing agents for the process provide a source of oxygen atoms to oxidize the p-xylene and/or p-toluic acid, and/or another intermediate oxidization product at the oxidation conditions employed. Examples of oxidizing agents include peroxides, superoxides, and nitrogen compounds containing oxygen such as nitric acids. In an embodiment, the oxidizing agent is a gas comprising oxygen, e.g. air, carbon dioxide, and molecular oxygen. The gas may be a mixture of gases. The amount of oxygen used in the process is preferably in excess of the stoichiometric amount required for the desired oxidation process. In an embodiment, the amount of oxygen contacted with the mixture ranges from about 1.2 times the stoichiometric amount to about 100 times the stoichiometric amount. Optionally, the amount of oxygen contacted with the mixture may range from about 2 times the stoichiometric amount to about 30 times the stoichiometric amount.

At least a portion of the components provides a liquid phase, although dissolution of one or more of the mixture components may not be complete at any, or some, time during the process. The liquid phase may be formed by mixing the components at ambient conditions. In another embodiment, the liquid phase is formed as the temperature of the mixture is raised, e.g., to about 100° C. to about 240° C. A mixture of the components may be formed prior to the oxidation step, in the same or different vessel as that used in the oxidation step. In another embodiment, a mixture of the components is formed in an oxidation reactor, e.g. adding various streams of the components individually and/or in combination to a continuous or semi-continuous oxidation reactor. The combined components and/or various streams of the components may be heated before they are mixed together or mixed before they are heated, as desired.

Though many conventional alkyl aromatic oxidation processes are typically conducted in a mixed phase, and often include three phases (e.g. solid, gas, and liquid), they are frequently referred to in the art as "liquid phase" oxidation processes because the oxidation conditions are maintained to provide at least a portion of the mixture in the liquid phase. It is also known in the art that the number of phases present may vary over time during the process. Processes according to the instant invention may also be conducted in a liquid phase or mixed phase in a similar manner as known in the art.

Conventional, liquid phase oxidation reactors as known in the art may be used to practice the invention. Examples include vessels, which may have one or more mechanical agitators, and various bubble column reactors such as those described in U.S. Pat. No. 7,692,036. It is also known to design, operate, and control such reactors and the oxidation reaction for the oxidation conditions employed including, e.g., the temperature, pressure, liquid and gas volumes, and corrosive nature of the liquid and gas phases where applicable. See, e.g. U.S. Pat. No. 7,692,036 and U.S. Pat. No. 6,137,001.

The oxidation temperature, pressure and residence time may vary based on a variety of factors including for example, the reactor configuration, size, and whether the process is, batch, continuous, or semi-continuous. An oxidation condition may also vary based on other oxidation conditions. For example, use of a particular temperature range may enable use of a different residence time range.

In an embodiment, the terephthalic acid produced by the instant invention may precipitate, crystallize, or solidify in a liquid phase mixture at the oxidation conditions and/or as the mixture cools. Thus, a mixture according to the invention may further comprise solid terephthalic acid. Other compounds, including color bodies, and other oxidation products may solidify with or be trapped in the solid oxidation product thus reducing the purity of the desired product. In an embodiment, the mixture comprises a liquid phase. The mixture may comprise a gas phase such as when the oxidizing agent is added as a gas. The mixture may comprise a solid phase e.g. a mixture component, an oxidation product, or a by-product fails to dissolve or solidifies in the mixture. In an embodiment, the mixture comprises a liquid phase, a solid phase and optionally a gas phase. In another embodiment, the mixture comprises a liquid phase and a gas phase.

As noted above and discussed below, it has been discovered that the invention may be used to produce an oxidation product having different amounts of contaminants relative to those observed in conventional processes. In addition, the invention provides new ways to control the level of various contaminants in the oxidation product. In an embodiment, a process according to the invention further comprises forming the oxidation product as a solid, optionally at the oxidizing conditions, to produce the solid oxidation product and a mother liquor. The solid oxidation product may be separated from the mother liquor, i.e. liquid phase, and the mother liquor of the process may be recycled and reused in the contacting step or other steps of the process described below.

Processes according to the invention may comprise one or more additional optional oxidizing steps. In an embodiment, a second oxidation step includes a second oxidizing temperature that is lower than the temperature of the first oxidizing step. Processes according to the invention may include additional contacting steps of the invention as described herein, and/or the invention may be combined with other oxidizing steps such as conventional oxidizing steps known in the art. Multiple contacting and/or oxidation steps may be conducted in series and/or parallel and may be combined with other process steps such as purification steps described herein.

In another embodiment, the invention further comprises purifying the oxidation product. Purifying may comprise one or more additional steps to isolate and purify the oxidation product. Examples of purifying steps include: separating wherein the oxidation product is separated from the mother liquor or another liquid phase such as by filtration and/or centrifugation; washing wherein the oxidation product is washed, for example with water and/or another solvent component; and drying the oxidation product. Such additional processing steps have been described in the general literature and are well known to those of ordinary skill in the art to be used in various combinations to purify oxidation products of the invention. See for example, the references cited in this application and the art cited therein.

A purification step of the instant invention may further comprise one or more solvent contacting steps. A solvent contacting step comprises contacting an oxidation product, also including washed or dried solid oxidation products, with a third solvent comprising at least one of water, a carboxylic acid, an ionic liquid and/or ionic liquid precursor, and a mother liquor to produce a purified oxidation product. In an embodiment, the solvent of the solvent contacting step contains ionic liquid and carboxylic acid, and optionally mother liquor. The composition of the solvent for the solvent contacting step can be as described above for the contacting step.

Solvent contacting may leach impurities from the solid oxidation product, and/or the oxidation product may be partially or completely dissolved in the solvent. Solvent contacting conditions include a solvent contacting temperature. The solvent contacting temperature may be lower than the oxidation temperature. In an embodiment, the solvent contacting temperature is at least 20° C. lower than the oxidation temperature. Solvent contacting may be practiced for example in the one or more crystallizers that follow the oxidation reactor in some conventional processes. The oxidation product may solidify, precipitate, or crystallize in the solvent of the solvent contacting step.

The product made by the process, either initially or following one or more additional oxidizing and/or purification steps, can contain less than about 2500 ppm 4-CBA, or less than about 2000 ppm 4-CBA, or less than about 1500 ppm 4-CBA, or less than about 1000 ppm 4-CBA, or less than about 750 ppm 4-CBA, or less than about 500 ppm 4-CBA, or less than about 250 ppm 4-CBA, or less than about 100 ppm 4-CBA, or less than about 50 ppm 4-CBA, or less than about 25 ppm 4-CBA.

EXAMPLE

A 500 ml Titanium autoclave provided by Parr Instrument was used. It was fitted with a standard Parr mixer typically operated at 950 rpm, with internal baffles installed to avoid vortex formation. An external water-cooled Parr condenser was used to reduce the vapor to 10° C. before reflux back to the reactor. A continuous online GC was installed after a guard ice trap, to measure the reactor off gas composition. A dipleg was installed for multiple purposes: to provide air to the reaction, to purge with Nitrogen, and to be used for composite sampling collection.

Two samplers were used for different purposes. A custom Titanium sampler was fabricated by Parr Instrument with a 2 μm Titanium filter included to separate solid and liquid phase at operating temperature for studying reaction kinetics. A custom Titanium sampler, larger in size but with no filter attached, was used for a solubility study.

The experiment is reactor-only batch-mode operation. For the kinetic study, a predetermined amount of reactant, solvent, and catalyst was loaded in the reactor. After a nitrogen pressure test at room temperature, the reactor was gradually heated up to the desired operating temperature. Air was slowly introduced, and the temperature was closely monitored for exotherm. Samples were taken at various sampling points, based on reaction time. Air was cut off to temporarily halt the reaction when samples were extracted.

For the solubility study, the solvent and solute were loaded in the reactor and heated to the desired temperature, and maintained for a certain time to ensure an equilibrium was established. Afterwards, sufficient time was allowed for the solid to settle before a sample was taken. Solubility was compared to another study that tested terephthalic acid solubility in acetic acid.

Figure 4:
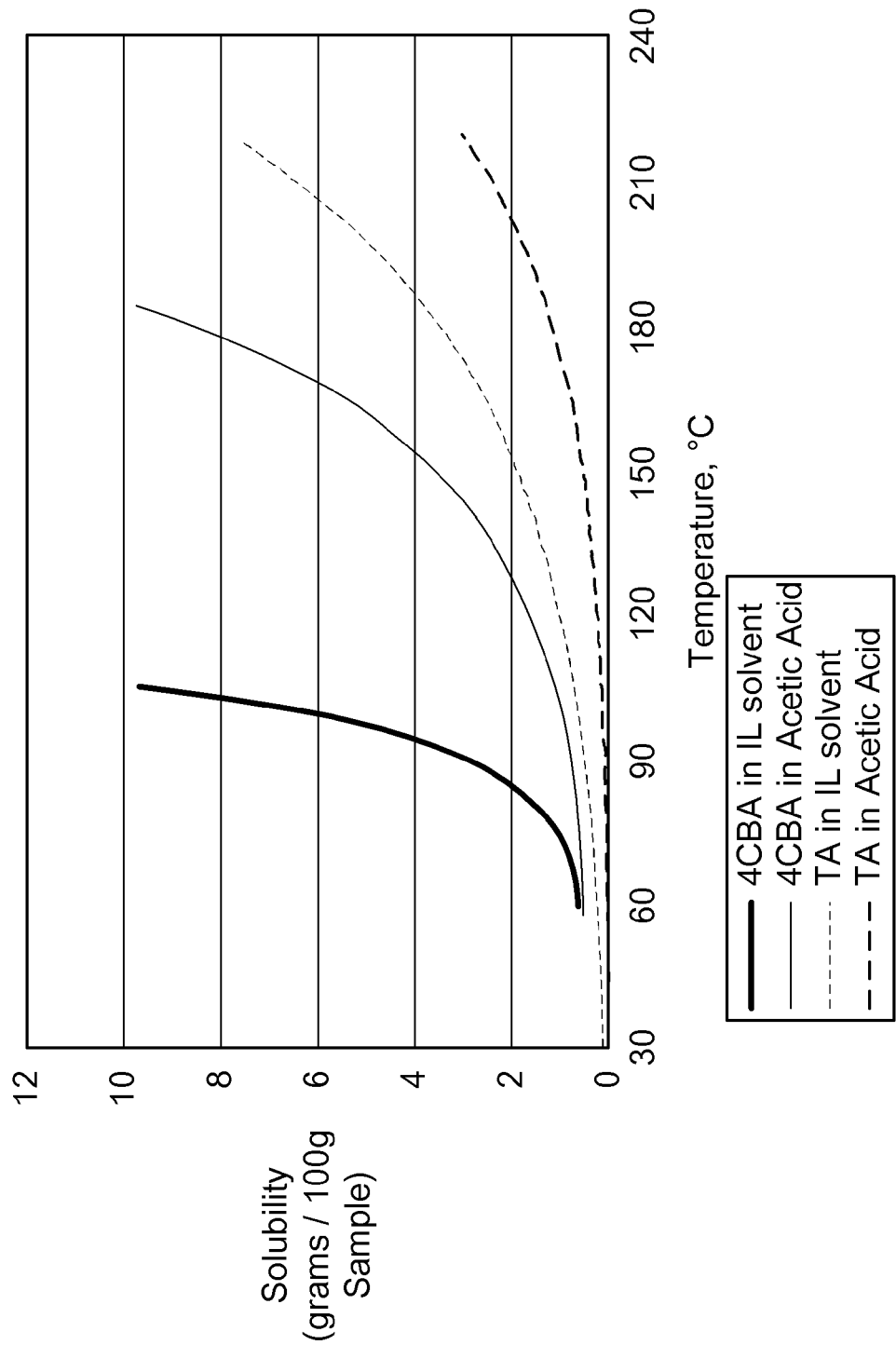
FIG. 4 is a graph showing the solubility of terephthalic acid and 4-CBA in acetic acid and ionic liquid solvent.

The results are shown FIG. 4. Both terephthalic acid and 4-CBA had greater solubility in ionic liquid than in acetic acid. The 4-CBA curves are estimated based on experimental and literature data.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed:

1. A process for oxidizing an alkyl aromatic compound comprising:
    contacting the alkyl aromatic compound, a first solvent comprising at least one of a first ionic liquid solvent and a first carboxylic acid solvent having a ratio of the first ionic liquid solvent to the first carboxylic acid solvent in a range of 0.1:1 to 10:1, a first bromine source, a first catalyst, and a first oxidizing agent in a first reaction zone at a temperature of about 240° C. or less and a pressure in a range of about 0.69 MPa(g) (100 psig) to about 4.1 MPa(g) (600 psig) for less than about 90 min to produce a first oxidation product comprising aromatic carboxylic acid, and at least one of unoxidized alkyl aromatic compound or partially oxidized alkyl aromatic compound, at least 50% of the aromatic carboxylic acid remaining in solution;

introducing the first oxidation product into a first crystallization zone;

controlling a composition of solvent in the first crystallization zone to maintain at least one of unoxidized alkyl aromatic compound or partially oxidized alkyl aromatic compound in solution; and crystallizing at least a portion of the aromatic carboxylic acid in the first crystallization zone to produce a first crystallized aromatic carboxylic acid and a first mother liquor comprising the first crystallization zone solvent and the at least one of unoxidized alkyl aromatic compound or partially oxidized alkyl aromatic compound and optionally aromatic carboxylic acid in solution, the first crystallization zone being at a temperature of about 220° C. or less and a pressure in a range of about 0 MPa(g) (0 psig) to about 2.1 MPa(g) (300 psig).

2. The process of claim 1, separating the first crystallized aromatic carboxylic acid from the first mother liquor.

3. The process of claim 1, further comprising recycling at least a portion of the first mother liquor to the first reaction zone.

4. The process of claim 1 wherein the first carboxylic acid solvent is acetic acid.

5. The process of claim 1 wherein the first ionic liquid solvent comprises a mixture of at least two ionic liquids.

6. The method of claim 1 further comprising;

contacting at least a portion of the first mother liquor, a second solvent, a second bromine source, a second catalyst, and a second oxidizing agent in a second reaction zone to produce a second oxidation product comprising aromatic carboxylic acid at a temperature of about 240° C. or less, and a pressure of about 0.69 MPa(g) (100 psig) to about 4.1 MPa(g) (600 psig);

crystallizing at least a portion of the aromatic carboxylic acid in a second crystallization zone to produce a second crystallized aromatic carboxylic acid and a second mother liquor comprising the first mother liquor and the second solvent, and optionally unoxidized alkyl aromatic compound, partially oxidized alkyl aromatic compound, and aromatic carboxylic acid in solution, the second crystallization zone being at a temperature of about 200° C. or less, and a pressure in a range of about 0 MPa(g) (0 psig) to about 2.1 MPa(g) (300 psig).

7. The process of claim 6, separating the second crystallized aromatic carboxylic acid from the second mother liquor.

8. The process of claim 6, further comprising recycling at least a portion of the second mother liquor to the first reaction zone, the second reaction zone, or both.

9. The process of claim 6, wherein the second solvent comprises at least one of a second ionic liquid solvent and a second carboxylic acid solvent.

10. The process of claim 9, wherein the second solvent has a ratio of the second ionic liquid solvent to the second carboxylic acid solvent in a range of 0.1:1 to 10:1.

11. The process of claim 9 wherein the second carboxylic acid solvent is acetic acid.

12. The process of claim 9 wherein the second ionic liquid solvent comprises a mixture of at least two ionic liquids.

13. The method of claim 1 further comprising: before contacting the alkyl aromatic compound, the first solvent, the first bromine source, the first catalyst, and the first oxidizing agent; contacting the alkyl aromatic compound, a third solvent not including an ionic liquid, a third bromine source, a third catalyst, and a oxidizing agent.

14. The process of claim 1 wherein the first reaction zone comprises a continuous stirred tank reactor, and wherein a ratio of the first solvent to the alkyl aromatic compound in the first reaction zone is in a range of about 1:1 to about 10:1.

15. The process of claim 1 wherein the first reaction zone comprises a plug-flow reactor, and wherein a ratio of first solvent to the alkyl aromatic compound in the first reaction zone is up to about 10:1.

16. The process of claim 1 wherein at least 90% of the aromatic carboxylic acid remains in solution in the first reaction zone.

17. The process of claim 1 wherein the alkyl aromatic compound, the first solvent, the first bromine source, the first catalyst, and the first oxidizing agent are contacted for less than 45 min.

18. The process of claim 1 wherein the alkyl aromatic compound is para-xylene, and the aromatic carboxylic acid is terephthalic acid.

* * * * *